United States Patent [19]

Komai et al.

[11] Patent Number: 5,078,750
[45] Date of Patent: Jan. 7, 1992

[54] HAIR DYEING BY IRIDOID GLYCOSIDES AND AGLYCONS THEREOF

[75] Inventors: Koichiro Komai, Kyoto; Shoichi Harima, Osaka, both of Japan

[73] Assignee: Tokiwa Kanpo Pharmaceutical Co., Ltd., Osaka, Japan

[21] Appl. No.: 650,615

[22] Filed: Feb. 1, 1991

[30] Foreign Application Priority Data

Feb. 2, 1990 [JP] Japan .................................. 2-24836

[51] Int. Cl.$^5$ .............................................. A61K 7/13
[52] U.S. Cl. ............................................ 8/405; 8/406; 8/409; 8/410; 424/70
[58] Field of Search ................... 8/405, 406, 428, 429, 8/409, 410; 424/70; 138/32

[56] References Cited

U.S. PATENT DOCUMENTS 4,247,698 1/1981 Toyama et al. ........................ 8/401
4,347,356 8/1982 Touyama et al. ...................... 8/568

*Primary Examiner*—Paul Lieberman
*Assistant Examiner*—William S. Parks

[57] ABSTRACT

A method of dyeing hair which comprises contacting hair with an iridoid glycoside or an aglycon thereof.

5 Claims, No Drawings

HAIR DYEING BY IRIDOID GLYCOSIDES AND AGLYCONS THEREOF

BACKGROUND OF THE INVENTION

1. Field of the Invention

The present invention relates to hair dyeing by iridoid glycosides and aglycons thereof. More particularly, the present invention provides a method of dyeing hair by a naturally occuring iridoid glycoside, an aglycon thereof or a semisynthetic analog of said glycoside, and a composition for use in such method.

2. Background Information

Various dyes have been used for dyeing white hair or for changing color of hair. Among such dyes, the most widely used are the oxidative hair dyes, the active component of which has, however, sensitizing and toxic properties and thus necessitate care in actual application. Organic and inorganic pigments have also been used. These are, however, easily removed on washing hair and repeated dyeing would be necessary. Another examples used for dyeing hair are acid dyes which require dyeing assistant such as benzyl alcohol in order to improve dyeing efficacy. Anyway, the conventional dyes are not satisfactory in safety requirements for application onto human hair.

Further, when the conventional dyes are used for dyeing hair, a considerably long time such as more than one hour is required for dyeing (including washing). In addition, finish of dyeing at the border of the hair is uneven and white hairs appear unevenly. Simple applying of pigment, so-called fashionable hair dyeing, is certainly easy but the applied pigment can be easily come loose and fall by touching with hand. In contrast, according to the present invention, long-lasting dyeing can be attained by simple dyeing procedure such as once or twice a day applying of the invented composition and a good finish of dyeing is obtained at the border of the hair.

While it has been known that the iridoid glycosides react with primary amines to form color substances and that such substances can be used for coloring foods, medicaments or cosmetics (for example, JP-A-53934/1977, JP-A-155259/1982, JP-A-125573/1988 and 19234/1986), it has not been known that the iridoid glycosides themselves can be used for dyeing hair.

SUMMARY OF THE INVENTION

In the first aspect, the present invention provides a method of dyeing hair which comprises contacting hair with an iridoid glycoside or an aglycon thereof.

In the second aspect, the present invention provides a use of an iridoid glycoside or an aglycon thereof for the manufacture of a cosmetic for dyeing hair.

In the third aspect, the present invention provides a cosmetic composition for dyeing fair comprising an iridoid glycoside or an aglycon thereof in association with a cosmetically acceptable carrier.

DETAILED DESCRIPTION OF THE INVENTION

As used herein, the term "iridoid glycosides" refers to compounds that have a monoterpene ring (1,4a,5 or 7,7a-tetrahydrocyclopenta[c]pyran) based on the 1-isopropyl-2,3-dimethylcyclopentane ring system as the nucleus and one or more sugar residue ethereally bound thereto. Said compounds include naturally occurring products obtained from plants belonging to Rubiaceae, Euphorbiaceae, Valerinaceae, Cornaceae, Gentianaceae, Caprifoliaceae, Oleaceae, Ericaceae, Loganiaceae, etc. and also semi-synthetic compounds prepared by binding (for example, enzymatically) one or more sugar unit to the natural product or aglycon thereof.

Said iridoid glycosides include compounds having a carboxylic acid or ester such as lower alkyl ester or lactone on the carbon atom at position 4 (such as asperuloside, deacetylasperuloside methyl ester, geniposide, geniposidic acid, monotropein, loganin and allamandin), compounds having a formyl group on the same atom (such as tarennoside), compounds having a hydroxymethyl group on the same atom (such as valtrate and ebuloside), compounds having a methyl group on the same atom (such as lamioside and strictoside) and compounds lacking such groups (such as aucubin and unedoside).

Representative examples of the iridoid glycosides include the following compounds.

Asperuloside: $C_{18}H_{22}O_{11}$, obtained from *Galium spurium* var. echinospermon and *Paederia scandens* var. Mairei of Rubiaceae, *Daphniphyrium macropodum* of Euphorbiaceae etc.

Paederoside: $C_{18}H_{22}O_{10}S$, obtained from *Paedria scandens* var. Mairei etc.

Geniposide: $C_{17}H_{24}O_{10}$, obtained from *Gardenia jasminoides* of Rubiaceae, *Cornus controversa, Cormus officinalis* of Cornaceae etc.

Geniposidic acid: $C_{16}H_{22}O_{10}$, obtained from *Daphniphylium macropodum* of Euphorbiaceae, *Paederia scandens* var. Mairei of Rubiaceae The aglycon is genipin.

Gardenoside: $C_{17}H_{24}O_{11}$, obtained from *Gardenia jasminoides* of Rubiaceae, *Daphniphylium macropodum* of Euphorbiaceae etc.

Monotropein: $C_{16}H_{22}O_{11}$, obtained from *Monotropa hypopitis, Vaccinium aliginosum, Vaccinium hirtum, Vaccinium Vitis-Idaea* of Ericaceae etc.

Kanokoside A: $C_{21}H_{32}O_{12}$; Kanokoside B: $C_{21}H_{34}O_{12}$; Kanokoside C: $C_{27}H_{42}O_{17}$; Kanokoside D: $C_{27}H_{43}O_{16}$, obtained from *Valeriana Fauriei, Valeriana flaccidissima* of Valerianaceae etc.

Aucubin: $C_{15}H_{22}O_9$, obtained from *Aucuba japonica* of Cornaceae etc.

Scandoside: $C_{16}H_{22}O_{11}$, obtained from *Paederia scandens* var. Mairei of Rubiaceae etc.

Sweroside: $C_{16}H_{22}O_9$, obtained from a plant of Loganiaceae, *Swertia japonica* of Gentianaceae etc.

Swertiamarin: $C_{16}H_{22}O_{11}$, obtained from *Swertia japonica* of Gentianaceae etc.

Loniceroside: $C_{17}H_{24}O_{10}$, obtained from *Lonicera japonica* of Caprifoliaceae etc.

Gentioflavoside: $C_{16}H_{22}O_{10}$, obtained from *Gentiana scabra* of Gentianaceae etc.

Villoside: $C_{16}H_{26}O_8$, obtained from *Petrinia scabiosaefolia* of Valerianaceae etc.

Syringenone: $C_{17}H_{24}O_9$, obtained from *Syringa reticulata* of Oleaceae etc.

Syringoxide: $C_{17}H_{24}O_{10}$, obtained from *Syringa reticulata* of Oleaceae etc.

These glycosides can generally be obtained by extracting a plant containing the glycosides with water or an organic solvent (for example, a hydrophilic solvent) and treating the extract by a conventional separating method, such as for example, concentrating, filtering, fractional crystallization, chromatography, solvent extraction, countercurrent extraction etc. or a combination thereof.

The iridoid glycosides also include modified glycosides based on the above exemplified glycoside. These modified glycosides include oxidized products, reduced products, deacylated products, acylated (for example, acetylated) products, esterified (for example, with lower alcohol) products, etherified products, amidated products etc. of the parent compounds. These can be prepared by the methods conventional for modifying the naturally occurring compounds.

The term "aglycon" refers to compounds corresponding to de-glycosilated parts of the iridoid glycosides as illustrated above. These aglycons can be obtained by hydrolyzing the iridoid glycosides with an acid, an alkali or an enzyme such as glycosidases. Representative examples of the aglycon include the following compounds.

Genipin: the aglycon of geniposide
Aucubigenin: the aglycon of aucubin
Eucomiol: the aglycon of aucubin According to the present invention, the iridoid glycoside and the aglycon can be used for the manufacture of cosmetics for dyeing hair. The cosmetics for dyeing hair means a composition for dyeing hair or changing or altering color of hair comprising, as an active ingredient, at least one iridoid glycoside or aglycon thereof in a cosmetically acceptable carrier. Such composition may be in the form of any cosmetics for hair including solid (for example, powders, granules, tablets etc. for ready to use in the preparation of a solution), liquid (such as a solution) and a combination thereof. Such combination may comprise a solution of an iridoid gylcoside as the first solution and a solution of acid as the second solution to be mixed with the first solution in order to hydrolyze the iridoid glycoside to the corresponding aglycon. These solutions may contain solubilizers, stabilizers, pH-adjusters, preservatives etc.

In the present invention, the cosmetics for hair means any cosmetics to be applied onto hair and may include solid and liquid preparations (including products for spraying), for example, hair restoration goods, oily hair dressings (for example, pomade, hair stick, hair oil etc.), emulsion hair dressings (hair cream, hair solid etc.), liquid hair dressings (hair liquid etc.), resinlike hair dressings (set lotion, hair-styling gel, water grease etc.), blow hair dressings (hair blow, hair mist etc.), hair spray, hair mousse, aerosol dressings, permanent wave solution, shampoo, rinse, hair pack etc. These hair cosmetics may include, in addition to the active ingredient, vegetable oils, mineral oils, synthetic oils, waxes, fatty acids, higher alcohols or esters thereof, hydrocarbons, surfactants, high molecular resins, amino acids or salts or esters thereof, polyhydric alcohols, organic solvents, resins, humectants, preservatives, antimycotics antioxidants, UV-absorbents, vitamins, hormones, antiperspirants, colorants, perfumes, water, properants etc. as the base. The cosmetic can be produced according to the conventional processes and stored or presented in usual containers or packages made out of glass, plastic, metal, paper, composite materials etc.

The amount of the glycosides or aglycons to be compounded in the cosmetic composition according to the present invention is usually 0.01–20% and preferably 0.1–10% based on the total weight of the composition.

According to the present invention, it has been discovered that the iridoid glycosides and aglycons thereof as illustrated above can react with compounds contained in hair and having functional groups such as amino or hydroxy group in the very state of being contained in hair to produce color substances of various tone of color. Accordingly, the glycosides and aglycons can be used to give a wide variety of colors to hair. Such colors include black, dark purple, purple, light purple, blue purple, blue, green, yellow green, gold, orange, brown, dark brown, light brown, gray etc. The dyeing according to the invention has a high fastness and stable for a long time by one dyeing. Further, side-effects such as skin irritation, skin rash and hair damage are rare or slight.

Following preparations and examples are given for explanation of this invention in more detail, while test examples are offered to clarify the effects of this invention.

PREPARATION 1 (IRIDOID GLYCOSIDE)

Leaves of *Daphniphylium macropodum* (4.0 kg) were crushed and extracted with methanol (17l). The extracted mixture was filtered with suction, and methanol was distilled off from the filtrate under reduced pressure. The residue was absorbed on 700 g of activated charcoal (chromatographic grade) and developed with distilled water as the first developing solvent, 20% methanol as the second developing solvent and methanol as the third developing solvent. The methanol fraction was concentrated under reduced pressure to give crystals, which were filtered to afford 33.2 g of Asperuloside. The filtrate was concentrated under reduced pressure, and the residue was subjected to chromatography on silica gel (Waco Gel C-300) (300 g) eluting with chloroform/methanol. The eluate was concentrated under reduced pressure to give 4.4 g of geniposidic acid.

PREPARATION 2 (IRIDOID GLYCOSIDE)

Fruits of gardenia (Gardinia jasminosides, 4.5 kg) were crushed and extracted with methanol (14l). The extracted mixture was filtered with suction, and methanol was distilled off from the filtrate under reduced pressure. The residue was extracted with ethyl acetate (5l) and the aqueous layer was concentrated under reduced pressure. The residue was absorbed on 700 g of activated charcoal chromatographic grade) and developed with distilled water as the first developing solvent, 20% methanol as the second developing solvent and methanol as the third developing solvent. The methanol fraction was concentrated under reduced pressure, subjected to chromatography on silica gel (Waco Gel C-300) (300 g) eluting with chloroform/methanol. The eluate was concentrated under reduced pressure to give 22.5 g of geniposide.

PREPARATION 3 (IRIDOID GLYCOSIDE)

Bedstraws (Galium sprium var. echinosperomon, 32.8 kg) were finely divided and extracted with methanol (128l) for three weeks in a constant temperature room at 5° C. After the extract was filtered, the filtrate was concentrated on a rotary evaporator. On Subjecting the concentrate to chromatography on activated charcoal column (700 g activated carbon, eluting with developing solvents: water, 20% methanol, 100% methanol in this order) and subjecting each fraction to TLC (plate: DC-Fertigplatten Kiesel gel 60$F_{254}$, Merck Co., developing solvent: chloroform:methanol:water=6:6:1, visualized with 50%-sulfuric acid), there was observed a component showing blue-violet spots in 100% methanol fraction. Then, 100% methanol fraction was concentrated under reduced pressure and cooled to give white needles. They were recrystallized from methanol to afford 68.0 g of Asperuloside.

TLC Rf=0.84, blue-violet
mp 128.5°-130° C.
UV $\lambda_{Max}^{MeOH}$ nm: 234
IR $\nu_{max}^{KBr}$ cm$^{-1}$: 3300, 1758, 1739

PREPARATION 4 (IRIDOID GLYCOSIDE)

Fruits of aucuba (*Aucuba japonica*, 750 g) were crushed with methanol and extracted with methanol. The extract was concentrated under reduced pressure and purified by column chromatography on activated charcoal. The development with water, 20% aqueous methanol and 100% methanol showed the presence of the glycoside in 100% methanol fraction, which was concentrated under reduced pressure. The glycoside was purified by silica gel column chromatography using chloroform-methanol system as a developing solvent to give aucubin as pale yellow crystals (yield 10.9 g).

The results of instrumental analysis of the isolated aucubin were shown below:

mp 181°-183° C.
UV $\lambda_{max}^{MeOH}$ nm: 210
IR $\nu_{max}^{KBr}$ cm$^{-1}$: 3300-3500, 1700, 1650

PREPARATION 5 (METHYL ESTER)

Asperuloside (1.0 g) was dissolved in distilled water (10 ml) and adjusted to pH=10 by adding a small amount of a saturated solution of BaO in methanol. This solution was allowed to stand for a few minutes to become cloudy white, which, after neutralization and concentration, was treated by silica gel column chromatography (Waco Gel C-300, 50 g, solvent: chloroform-methanol system). Silica gel column chromatography gave deacetyl asperulosidic acid methyl ester having Rf value=0.79 (chloroform-methanol-water=6:6:1, visualized with 50(%)-sulfuric acid) on TLC, as white needles (1.80 mg).

TLC Rf=0.79, blue-violet
mp 130°-132° C.
UV $\lambda_{max}^{MeOH}$ nm: 32
IR $\nu_{max}^{KBr}$ cm$^{-1}$: 3200-3300, 1690, 1630
FAB-MS M+Na=427

PREPARATION 6 (AGLYCON)

To a solution of geniposide (6.5 g) dissolved in distilled water (65 ml), was added β-glucosidase (No.G-0395, β-D-glucoside glucohydrase EC 3.2.1.21) (316.55 mg, 1677.72 units) the mixture was incubated at 37° C. for 4.5 hours. The progress of the reaction was monitored by TLC (chloroform:methanol=8:2, visualized with 50%-sulfuric acid). After the reaction was complete, the reaction solution was extracted several times with ethyl acetate, and subsequently the ethyl acetate layer was concentrated to give genipin as white needles (2.55 g, yield 67.3%).

TLC Rf=0.79, dark brown
mp 119°-121° C.
UV $\lambda_{max}^{MeOH}$ nm: 238
IR $\nu_{max}^{KBr}$ cm$^{-1}$: 3380, 3200, 2900, 1680, 1628

Example 1 (hair tonic)

| | | |
|---|---|---|
| (A) | polyoxyethylene polyoxypropylene decyl tetradecyl ether | 1.0 g |
| | pyridoxine dioctanoate | 0.05 |
| | ethanol | 55.0 |
| | methyl paraben | 0.1 |
| | Genipin | 5.0 |
| (B) | 1,3-butylene glycol | 2.0 |
| | purified water q.s. to | 100 g |

PREPARATION

A and B are dissolved separately and mixed together to produce a tonic.

Example 2 (hair tonic)

| | | |
|---|---|---|
| (A) | polyoxyethylene polyoxypropylene decyl tetradecyl ether | 1.0 g |
| | pyridoxine dioctanoate | 0.05 |
| | ethanol | 55.0 |
| | methyl paraben | 0.1 |
| (B) | 1,3-butylene glycol | 2.0 |
| | geniposidic acid | 5.0 |
| | purified water q.s. to | 100 g |

PREPARATION

A and B are dissolved separately and mixed together to produce a tonic.

Example 3 (hair liquid)

| | | |
|---|---|---|
| (A) | polyoxyethylene polyoxypropylene decyl tetradecyl ether | 0.3 g |
| | polyoxypropylene butyl ether | 18.0 |
| | ethanol | 50.0 |
| | methyl paraben | 0.1 |
| | Genipin | 3.0 |
| (B) | propylene glycol | 5.0 |
| | purified water q.s. to | 100 g |

PREPARATION

A and B are dissolved separately and mixed together to produce a liquid.

Example 4 (hair liquid)

| | | |
|---|---|---|
| (A) | polyoxyethylene polyoxypropylene decyl tetradecyl ether | 0.3 g |
| | polyoxypropylene butyl ether | 18.0 |
| | ethanol | 50.0 |
| | methyl paraben | 0.1 |
| (B) | propylene glycol | 5.0 |
| | Geniposide | 3.0 |
| | purified water q.s. to | 100 g |

PREPARATION

A and B are dissolved separately and mixed together to produce a liquid.

Example 5 (hair setting lotion)

| | | |
|---|---|---|
| (A) | polyvinylpyrrolidone | 2.0 g |
| | polyoxyethylene oleyl ether | 1.0 |
| | ethanol | 30.0 |
| | Genipin | 0.5 |
| (B) | glycerol | 2.0 |
| | purified water q.s. to | 100 g |

PREPARATION

A and B are dissolved separately and mixed together to produce a hair setting lotion.

Example 6 (hair setting lotion)

| (A) | polyvinylpyrrolidone | 2.0 g |
| --- | --- | --- |
|  | polyoxyethylene oleyl ether | 1.0 |
|  | ethanol | 30.0 |
| (B) | glycerol | 2.0 |
|  | Asperuloside | 0.5 |
|  | purified water q.s. to | 100 g |

PREPARATION

A and B are dissolved separately and mixed together to produce a hair setting lotion.

Example 7 (hair cream)

| (A) | bleached beeswax | 5.0 g |
| --- | --- | --- |
|  | glycerol monostearate | 3.0 |
|  | reduced lanolin | 1.5 |
|  | polyoxyethylene sorbitan monostearate | 3.0 |
|  | paraffin wax | 2.0 |
|  | liquid paraffin | 20.0 |
|  | camellia oil | 10.0 |
|  | Genipin | 2.0 |
| (B) | borax | 0.5 |
|  | glycerol | 3.0 |
|  | carboxyvinyl polymer | 0.2 |
|  | purified water q.s. to | 100 g |

PREPARATION

A and B are separately dissolved with heating to 70° C., and then, are emulsified by mixing. The resulting emulsion is cooled to give cream.

Example 8 (hair cream)

| (A) | bleached beeswax | 5.0 g |
| --- | --- | --- |
|  | glycerol monostearate | 3.0 |
|  | reduced lanolin | 1.5 |
|  | polyoxyethylene sorbitan monostearate | 3.0 |
|  | paraffin wax | 2.0 |
|  | liquid paraffin | 20.0 |
|  | camellia oil | 10.0 |
| (B) | borax | 0.5 |
|  | glycerol | 3.0 |
|  | carboxyvinyl polymer | 0.2 |
|  | Aucubin | 2.0 |
|  | purified water q.s. to | 100 g |

PREPARATION

A and B are separately dissolved with heating to 70° C., and then, are emulsified by mixing. The resulting emulsion is cooled to give cream.

Example 9 (pomade)

| Japan wax | 10.0 g |
| --- | --- |
| castor oil | 87.0 |
| hydrogenated oil | 2.0 |
| Genipin | 0.2 |

PREPARATION

Each gredient is mixed, heated to melt, and then cooled to give pomade.

Example 10 (hair shampoo)

| (A) | potassium coconut oil fatty acid hydrolysed collagen | 10.0 g |
| --- | --- | --- |
|  | polyoxyethylene alkyl ether sodium sulfate (3 E.O.) | 30.0 |
|  | polyoxyethylene hydrogenated castor oil (60 E.O.) | 1.0 |
|  | 2-alkyl-N-carboxymethyl-N-hydroxyethyl-imidazolinium betaine | 30.0 |
|  | 1,3-butylene glycol | 2.0 |
|  | dehydroacetic acid | 0.2 |
|  | Genipin | 8.0 |
| (B) | Leoguard G (10% aqueous solution) purified water q.s. to | 100 g |

PREPARATION

A and B are separately dissolved with heating, after which are mixed to give a shampoo.

Example 11 (hair shampoo)

| (A) | potassium coconut oil fatty acid hydrolysed collagen | 10.0 g |
| --- | --- | --- |
|  | polyoxyethylene alkyl ether sodium sulfate (3 E.O.) | 30.0 |
|  | polyoxyethylene hydrogenated castor oil (60 E.O.) | 1.0 |
|  | 2-alkyl-N-carboxymethyl-N-hydroxyethyl-imidazolinium betaine | 30.0 |
|  | 1,3-butylene glycol | 2.0 |
|  | dehydroacetic acid | 0.2 |
| (B) | Leoguard G (10% aqueous solution) |  |
|  | Loganin | 8.0 |
|  | purified water q.s. to | 100 g |

PREPARATION

A and B are separately dissolved with heating, after which are mixed to give a shampoo.

Example 12 (hair rinse)

| (A) | polyoxyethylene oleyl ether (7 E.O.) | 2.0 g |
| --- | --- | --- |
|  | benzalkonium chloride | 3.0 |
|  | distearyldimethylammonium chloride | 3.0 |
|  | hydrolysed collagen | 1.0 |
|  | 1,3-butylene glycol | 5.0 |
|  | Genipin | 4.0 |
| (B) | purified water q.s. to | 100 g |

PREPARATION

A and B are separately heated up to 75° C. A is added to B and they are emulsified by mixing. After cooling, a rinse is obtained.

Example 13 (hair rinse)

| (A) | polyoxyethylene oleyl ether (7 E.O.) | 2.0 g |
| --- | --- | --- |
|  | benzalkonium chloride | 3.0 |
|  | distearyldimethylammonium chloride | 3.0 |
|  | hydrolysed collagen | 1.0 |
|  | 1,3-butylene glycol | 5.0 |
| (B) | geniposidic acid | 4.0 |

-continued

| | |
|---|---|
| purified water q.s. to | 100 g |

PREPARATION

A and B are separately heated up to 75° C. A is added to B and they are emulsified by mixing. After cooling, a rinse is produced.

Example 14 (hair treatment pack)

| (A) | polyoxyethylene oleyl ether (2 E.O.) | 5.0 g |
|---|---|---|
| | stearyltrimethyl ammonium chloride | 5.0 |
| | deodorized cetanol | 6.0 |
| | anhydrous lanolin | 1.0 |
| | 2-octyldodecanol | 2.0 |
| | isopropyl myristate | 9.0 |
| | Genipin | 1.5 |
| (B) | purified water q.s. to | 100 g |

PREPARATION

A and B are separately heated up to 75° C. A is added to B and they are emulsified by mixing. After cooling, a hair treatment pack is produced.

Example 15 (hair treatment pack)

| (A) | polyoxyethylene oleyl ether (2 E.O.) | 5.0 g |
|---|---|---|
| | stearyltrimethyl ammonium chloride | 5.0 |
| | deodorized cetanol | 6.0 |
| | anhydrous lanolin | 1.0 |
| | 2-octyldodecanol | 2.0 |
| | isopropylmiristate | 9.0 |
| (B) | geniposide | 1.5 |
| | purified water q.s. to | 100 g |

PREPARATION

A and B are separately heated up to 75° C. A is added to B and they are emulsified by mixing. After cooling, a hair treatment pack is produced.

Test example 1 (hair dyeability test and dyeing color-fastness test)

1. Hair dyeability test

Human white hairs were soaked in a solution of 0.1-10% genipin in 50% ethanol for 24 hours and the dyeing of the hairs was visually judged. The results are shown in Table 1.

TABLE 1

| composition | concentration of genipin (%) | color |
|---|---|---|
| 1 | 0.1 | green |
| 2 | 1 | deep green-blue-green |
| 3 | 5 | blue-black-black |
| 4 | 10 | black |

2. Color-fastness test

The color of the hairs in above (1) after washing with shampoo was visually judged. The results are shown in Table 2 using the following symbols.

o: no change
Δ: little dye-bleeding
x: clearly dye-bleeding

TABLE 2

| composition | color-fastness |
|---|---|
| Comparative example 1 | Δ |
| Comparative example 2 | x |
| 1 | o |
| 2 | o |
| 3 | o |
| 4 | o |

Comparative example 1: soaked in 1% paraphenylenediamine solution for 30 minutes, followed by soak in 6% hydrogen peroxide.

Comparative example 2: soaked in 5% tannic acid solution for 24 hours, followed by soak in 5% ferric chloride solution for one hour.

Results

The compositions of the present invention showed superior dye-ability to the comparative ones.

Test example 2

1. Hair dyeability test

White hairs were dyed with a solution of 0.1-10% geniposic acid in 50% ethanol once or twice a day for 10 days and the dyeing of the hairs visually judged. The results are shown in Table 3.

TABLE 3

| composition | concentration of geniposidic acid (%) | color |
|---|---|---|
| 1' | 0.1 | light green |
| 2' | 1 | deep green-blue-green |
| 3' | 5 | blue-black-black |
| 4' | 10 | black |

2. Color-fastness test

Results similar to those in Test Example 1-2 are obtained using the composition 1', 2', 3' and 4'.

Similar results are obtained by using other iridoid glycosides which are known to form color products from primary amines in place of genipin or geniposidic acid in Test examples 1 and 2.

What we claim is:

1. A method of dyeing hair which comprises contacting hair with an iridoid glycoside or an aglycon thereof.

2. A method according to claim 1, in which the iridoid glycoside or the aglycon has a cyclopenta[c]pyran ring.

3. A method according to claim 2, in which the iridoid glycoside or the aglycon has a carboxy group or a lower alkyl ester thereof on the carbon atom at position 4 of the cyclopenta[c]pyran ring.

4. A method according to claim 3, in which the iridoid glycoside is geniposidic acid.

5. A method according to claim 3, in which the aglycon is genipin.

* * * * *